US00PP19589P3

(12) United States Plant Patent
Zaiger et al.

(10) Patent No.: US PP19,589 P3
(45) Date of Patent: Dec. 23, 2008

(54) CHERRY TREE NAMED 'ROYAL LYNN'

(50) Latin Name: *Prunus avium*
Varietal Denomination: Royal Lynn

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 173 days.

(21) Appl. No.: 11/656,024

(22) Filed: Jan. 22, 2007

(65) Prior Publication Data

US 2008/0184404 P1 Jul. 31, 2008

(51) Int. Cl.
*A01H 5/00* (2006.01)

(52) U.S. Cl. ..... Plt./181

(58) Field of Classification Search ..... Plt./181
See application file for complete search history.

*Primary Examiner*—Howard J Locker

(57) ABSTRACT

A new and distinct variety of cherry tree (*Prunus avium*). The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Fruit maturity in the early season.
2. Heavy and regular production of fruit.
3. Fruit with an attractive red skin color.
4. Early blooming with a low winter chilling requirement of approximately 500 hours at or below 45° F.
5. Fruit with good flavor and eating quality.
6. Firm fruit with good handling and storage ability.

1 Drawing Sheet

Botanical description: *Prunus avium.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Bing' Cherry (non-patented) and 'Royal Lee' Cherry (U.S. Plant Pat. No. 12,417).

ORIGIN OF THE VARIETY:

The present new variety of cherry tree (*Prunus avium*) was originated by us in our experimental orchard located near Modesto, Calif. as a first generation cross between our proprietary cherry tree '91LA460' and 'Royal Lee' Cherry (U.S. Plant Pat. No. 12,417). The maternal parent '91LA460' originated as a third generation cross of a selected proprietary seedling from an open pollinated 'Bing' Cherry tree (non-patented) and a low chilling cherry seedling of unknown parentage. A large group of these first generation crosses were budded on older trees of 'Mahaleb' Rootstock (non-patented) to accelerate earlier fruit production for evaluation. Under close and careful observation, one such seedling exhibited desirable fruit characteristics and was selected in 1998 for additional asexual propagation and commercialization.

ASEXUAL REPRODUCTION OF THE VARIETY:

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY:

The new and distinct cherry tree is of large size, vigorous upright growth, and has a low winter chilling requirement of approximately 500 hours below 45° F. The tree is a regular and productive bearer of medium to large size fruit with good flavor and eating quality. The fruit is further characterized by ripening in the early maturity season, having an attractive red skin color, with firm flesh, good storage and handling quality and its ability to remain firm on the tree 10 days past maturity (shipping ripe). In comparison to its maternal parent '91LA460' the fruit is larger in size and is 13 days earlier in maturity. In comparison to 'Royal Lee' Cherry (U.S. Plant Pat. No. 124,217) the fruit of the new variety is approximately 2 days earlier in maturity with slightly larger size fruit.

PHOTOGRAPH OF THE VARIETY:

The accompanying color photographic illustration shows typical specimens of the foliage and fruit of the present new cherry variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY:

The following is a detailed botanical description of the new variety of cherry tree, its flowers, foliage and fruit, as based on observations of a 10 year old specimen grown near Modesto, Calif., with color in accordance with Munsell Book of Color.

Tree:

*Size.*—Large. Pruned to 3.0 to 3.5 meters in height for economical harvesting of fruit. Average spread of 3.0 to 3.5 meters, varies with different cultural practices.

*Vigors.*—Vigorous, tree growth of 1.5 to 2 meters in height the first growing season. Growth rate will vary with types of soil, fertility and cultural practices.

*Form.*—Upright, usually pruned to vase shape.

*Branching habit.*—Semi spreading, crotch angle approximately 45°, increases with heavy crop load.

*Productivity.*—Productive. Produces heavy crop annually.

*Bearer.*—Regular. Has adequate fruit set annually. Set varies with climatic conditions at bloom time.

*Fertility.*—Self-sterile, pollinator required.

*Density.*—Medium dense, controlled by pruning.

*Hardiness.*—Tree grown in USDA Hardiness Zone 9. Hardy in all stone fruit growing areas in California. Winter chilling requirement is approximately 500 hours below 45° F.

Trunk:

*Size.*—Large. Average circumference of 48.3 cm at 30.5 cm above ground on a 10 year old tree.

*Stocky.*—Medium stocky.

*Texture.*—Medium rough, roughness increases with age of tree.

*Color.*—Varies from 10YR 3/4 to 2.5Y 7/2.

Branches:

*Size.*—Medium stocky. Average circumference 19.8 cm at 1.0 meter above ground. Crotch angle approximately 45°, increases with heavy crop load.

*Surface texture.*—New growth relatively smooth. Old growth medium rough, roughness increases with age of growth.

*Lenticels.*—Average 19 in a 25.8 sq cm area of branch. Average length 5.2 mm. Average width 1.8 mm. Color varies from 5YR 5/8 to 7.5YR 5/8.

*Color.*—New growth varies from 2.5GY 6/6 to 2.5GY 5/6. Old growth varies from 5YR 2/4 to 7.5YR 3/2, varies with age of growth.

Leaves:

*Size.*—Large. Average length 148.9 mm. Average width 69.3 mm.

*Form.*—Lanceolate.

*Apex.*—Acuminate.

*Base.*—Cuneate.

*Margin.*—Doubly serrate.

*Margin.*—Medium.

*Surface texture.*—Upper surface relatively smooth, slight indentations over midrib and leaf veins, glabrous. Lower surface relatively smooth, small ridges created by midrib and pinnate venation, glabrous.

*Petiole.*—Average length 28.0 mm. Average width 2.0 mm. Color varies from 5R 2/4 to 7.5R 2/6. Shallow longitudinal groove, glabrous.

*Glands.*—Reniform/size — large. Average length 2.0 mm. Average diameter 1.4 mm. Average number 3, varies from 1 to 4. Located primarily on upper portion of petiole. Color varies from 10R 3/10 to 7.5R 3/10.

*Color.*—Upper surface varies from 5GY 3/6 to 7.5GY 3/6. Lower surface varies from 5GY 5/4 to 5GY 4/4. Midvein color varies from 10Y 6/4 to 2.5GY 6/6.

*Flower buds:*

*Size.*—Large. Average length 18.6 mm. Average diameter 7.8 mm.

*Hardiness.*—Hard with respect to California winters.

*Form.*—Conical, becoming elongated before opening.

*Pedicel.*—Average length 15.3 mm. Average width 1.4 mm. Color varies from 5GY 7/8 to 5GY 6/6.

*Color.*—N 9.5/ (white), edged with 2.5R 7/4 to 2.5R 8/4 along upper surface of petals, color fades to white as buds open.

*Number of buds per spur.*—Average 8, varies from 5 to 11.

Flowers:

*Size.*—Large. Average height 21.5 mm. Average diameter 35.3 mm.

*Petals.*—Number 5, alternately arranged to sepals. Size — large. Average length 17.1 mm. Average width 16.2 mm. Form — orbicular. Margin — sinuate. Both surfaces glabrous. Color N 9.5/ (white).

*Sepals.*—Number 5, alternately arranged to petals. Size — medium. Average length 7.4 mm. Average width 5.3 mm. Shape — triangular. Margin — entire. Color — upper surface varies from 5GY 6/6 to 7.5GY 5/6. Lower surface varies from 5GY 6/6 to 5R 3/6. Both surfaces glabrous.

*Stamens.*—Average number per flower 35. Average filament length 15.1 mm. Filament color N 9.5/ (white). Anther color varies from 5Y 8.5/8 to 5Y 8/8.

*Pollen.*—Present, self-sterile, pollinator required. Color varies from 2.5Y 7/10 to 5Y 7/12.

*Pistil.*—Normally 1. Average length 15.9 mm. Surface glabrous. Position of stigma approximately 1.3 mm below anthers. Color varies from 2.5GY 7/6 to 5GY 7/6.

*Fragrance.*—Slight aroma.

*Blooming period.*—Date of First Bloom Feb. 24, 2005. Date of Petal Fall Mar. 5, 2005, varies slightly with climatic conditions. Color: N 9.5/ (white). Number Flowers per Flower Bud: Varies from 1 to 4, average 3. Pedicel: Average length 16.6 mm. Average width 1.4 mm. Color varies from 5GY 7/6 to 5GY 6/6.

Fruit:

*Maturity when described.*—Firm ripe.

*Date of first picking.*—May 2, 2005.

*Date of last picking.*—May 9, 2005, varies slightly with climatic conditions.

*Size.*—Medium to large. Average diameter axially 27.3 mm. Average transversely in suture plane 25.1 mm. Average weight 9.5 grams, varies slightly with fertility of the soil, amount of thinning and climatic conditions.

*Form.*—Globose to slightly elongated.

*Suture.*—Nearly smooth, extends from base to apex.

*Ventral surface.*—Nearly smooth.

*Apex.*—Rounded to slightly retuse.

*Base.*—Retuse.
*Cavity.*—Rounded. Average depth 1.4 mm. Average diameter 6.1 mm.

Stem:
*Size.*—Large. Average length 41.2 mm. Average diameter 1.4 mm.
*Color.*—Varies from 5GY 6/6 to 5GY 5/6.

Flesh:
*Ripens.*—Slightly earlier at the apex.
*Texture.*—Very firm.
*Fibers.*—Few, small, tender.
*Firmness.*—Very firm.
*Aroma.*—Moderate.
*Amydgalin.*—Undetected.
*Eating quality.*—Very good.
*Flavor.*—Very good, good balance between acid and sugar.
*Juice.*—Moderate amount, enhances flavor.
*Brix.*—Average 18.0°, varies slightly with amount of fruit per tree and climatic conditions.
*Color.*—Marbled, varies between 7.5Y 9/4 to 5R 3/8. Pit cavity varies between 5R 2/6 to 5R 3/8.

Skin:
*Thickness.*—Medium.
*Surface.*—Smooth.
*Bloom.*—Wanting.
*Tendency to crack.*—None during dry weather. Slight tendency to crack during wet weather, varies with stage of maturity.
*Color.*—Varies from 5R 3/10 to 5R 2/8.
*Tenacity.*—Tenacious to flesh.
*Astringency.*—Undetected.

Stone:
*Type.*—Clingstone.
*Size.*—Medium. Average length 14.2 mm. Average width 10.6 mm. Average thickness 7.7 mm.
*Form.*—Obovoid.
*Base.*—Flat to slightly rounded.
*Apex.*—Slight apical point. Average length 0.2 mm.
*Surface.*—Smooth. Small ridges running along each side of the suture line and extends slightly beyond base on some stones.
*Sides.*—Varies from equal to unequal with one side extending further from the suture plane.
*Tendency to split.*—None.
*Color.*—Varies from 10YR 6/4 to 10YR 6/6 when dry.

Kernal:
*Form.*—Ovate.
*Taste.*—Bitter.
*Viability.*—Partially viable, incomplete embryos in some stones. Average width 5.0 mm. Average depth 2.6 mm.
*Skin.*—Color varies from 10YR 8/4 to 2.5Y 9/2 when dry.

Use: Dessert. Market — local and long distance.

Keeping quality: Good, held firm in cold storage 2 weeks at 38° to 42° F. without internal breakdown of flesh, shriveling or appreciable loss of flavor.

Shipping quality: Good, showed minimal flesh bruising or skin scarring during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of cherry tree, substantially as illustrated and described, characterized by its large size, vigorous upright growth, having a low winter chilling requirement of approximately 500 hours at or below 45° F. and being a regular and productive bearer of medium to large size fruit that ripens in the early maturity season; the fruit is further characterized by its attractive red skin color, its firm flesh that has the ability to remain firm on the tree 10 days past maturity (shipping ripe) with good flavor and eating quality, and in comparison to its parent 'Royal Lee' Cherry (U.S. Plant Pat. No. 2,417) the fruit of the new variety is approximately 2 days earlier in maturity and slightly larger in size.

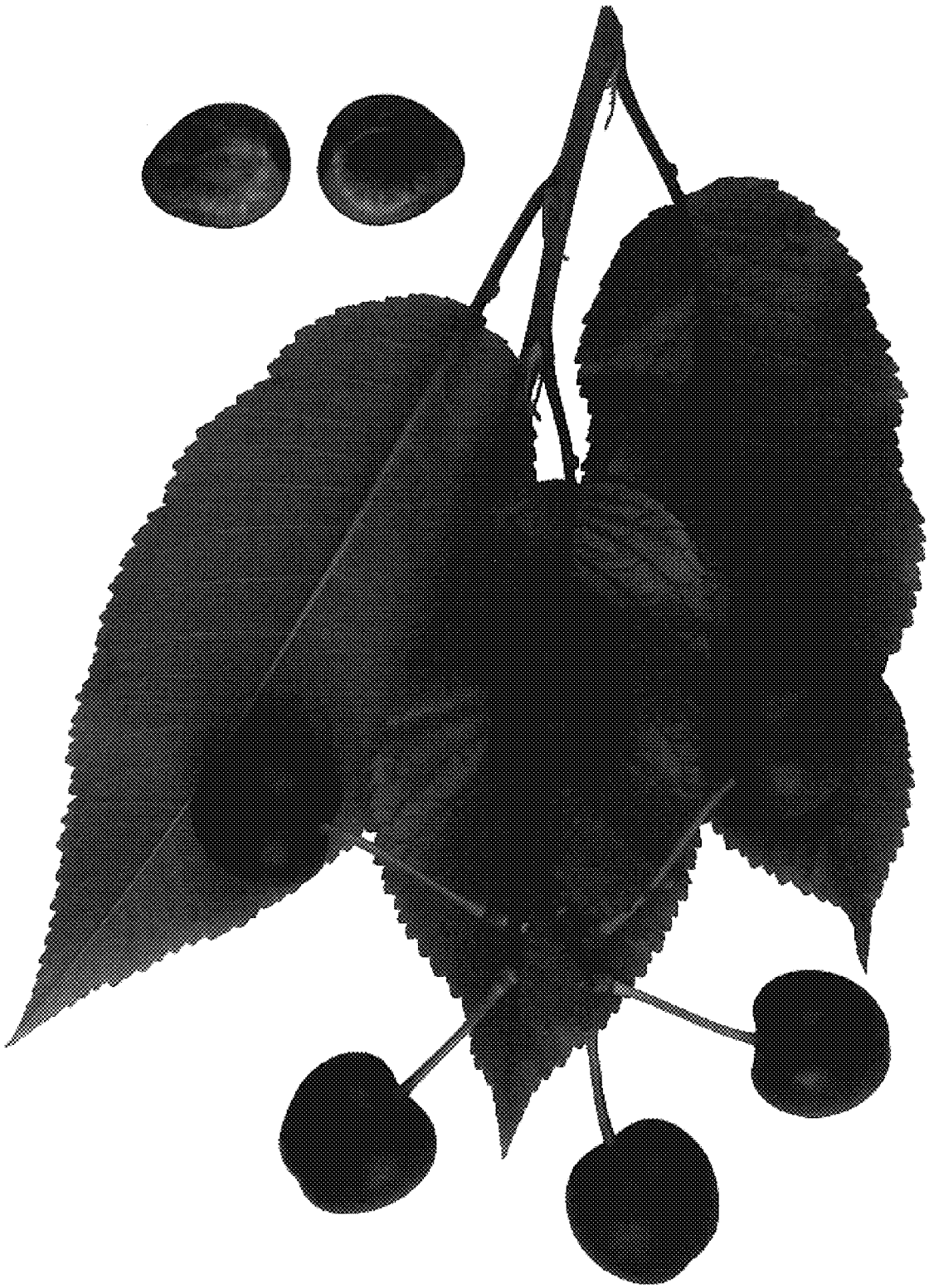

* * * * *